United States Patent
Pieske

(10) Patent No.: US 8,133,225 B2
(45) Date of Patent: Mar. 13, 2012

(54) IMPLANT FOR LONG BONES AND TREATMENT METHOD

(76) Inventor: Oliver Pieske, Germering (DE)

( * ) Notice: Subject to any disclaimer, the term of this patent is extended or adjusted under 35 U.S.C. 154(b) by 197 days.

(21) Appl. No.: 12/454,170

(22) Filed: May 12, 2009

(65) Prior Publication Data
US 2009/0287213 A1 Nov. 19, 2009

Related U.S. Application Data

(63) Continuation of application No. PCT/EP2006/011151, filed on Nov. 21, 2006.

(51) Int. Cl.
*A61B 17/72* (2006.01)
(52) U.S. Cl. .......................................................... 606/62
(58) Field of Classification Search .............. 606/62–68, 606/95, 99, 232; 623/13.14, 13.15
See application file for complete search history.

(56) References Cited

U.S. PATENT DOCUMENTS

| | | | |
|---|---|---|---|
| 3,977,398 A * | 8/1976 | Burstein | 606/62 |
| 5,034,012 A * | 7/1991 | Frigg | 606/62 |
| 5,053,035 A | 10/1991 | McLaren | |
| 5,470,334 A | 11/1995 | Ross et al. | |
| 5,836,949 A * | 11/1998 | Campbell et al. | 606/62 |
| 5,879,352 A * | 3/1999 | Filoso et al. | 606/62 |
| 6,045,551 A * | 4/2000 | Bonutti | 606/60 |
| 6,056,755 A | 5/2000 | Horas et al. | |
| 6,096,060 A | 8/2000 | Fitts et al. | |
| 6,267,767 B1 * | 7/2001 | Strobel et al. | 606/104 |
| 6,319,255 B1 | 11/2001 | Grundei et al. | |
| 6,524,313 B1 * | 2/2003 | Fassier et al. | 606/63 |
| 6,610,064 B1 * | 8/2003 | Goble et al. | 606/232 |
| 6,808,528 B2 * | 10/2004 | Justin | 606/916 |
| 7,101,376 B2 * | 9/2006 | Semet | 606/62 |
| 7,255,712 B1 * | 8/2007 | Steinberg | 623/16.11 |
| 7,575,603 B2 * | 8/2009 | Bergin et al. | 623/23.31 |

(Continued)

FOREIGN PATENT DOCUMENTS

DE 824 377 12/1951

(Continued)

OTHER PUBLICATIONS

XP-002443987 DATABASE WPI Week 198004, Derwent Publications Ltd., London, GB; AN 1980-A8866C (1 page).

(Continued)

*Primary Examiner* — Eduardo C Robert
*Assistant Examiner* — Jacqueline Johanas
(74) *Attorney, Agent, or Firm* — Lipsitz & McAllister, LLC

(57) ABSTRACT

The present application relates to an implant for tubular bones and to a method for treating fractures of tubular bones. The implant is used to connect two parts of a tubular bone that has broken with a substantially smooth break. The implant is formed by a shaped piece that is inserted into the medullary cavity of a broken tubular bone. The shaped piece has at least one through-opening, which has a substantially constant internal diameter and extends substantially through the shaped piece and through which a cord can be pulled in order to stabilize the fracture. The shaped piece is made of resorbable material, and two anchor parts can be secured on the cord. The anchor parts fix the cord to the bone, and the shaped piece exploits the principle of an internally braced stack in order to press the fracture surfaces of the bone against each other.

21 Claims, 9 Drawing Sheets

U.S. PATENT DOCUMENTS

| | | |
|---|---|---|
| 7,686,838 B2 * | 3/2010 | Wolf et al. .................... 606/325 |
| 2002/0188297 A1 * | 12/2002 | Dakin et al. .................... 606/72 |
| 2005/0027294 A1 | 2/2005 | Woll |
| 2005/0216007 A1 * | 9/2005 | Woll et al. ...................... 606/62 |
| 2006/0129153 A1 | 6/2006 | Klaue et al. |
| 2007/0213725 A1 * | 9/2007 | Hack .............................. 606/62 |

FOREIGN PATENT DOCUMENTS

| | | |
|---|---|---|
| DE | 1 852 874 | 6/1962 |
| DE | 26 57 303 | 6/1977 |
| DE | 36 30 138 | 3/1988 |
| DE | 196 18 552 | 11/1997 |
| EP | 0 428 985 | 5/1991 |
| FR | 2 721 818 | 5/1996 |
| WO | 98/26725 | 6/1998 |
| WO | 98/49962 | 11/1998 |
| WO | 2004/014243 | 2/2004 |
| WO | 2004/089255 | 10/2004 |

OTHER PUBLICATIONS

XP-002443905 DATABASE WPI Week 198512, Derwent Publications Ltd., London, GB; AN 1985-073545 (1 page).

* cited by examiner

Single Tooth Hook

IMPLANT FOR LONG BONES AND TREATMENT METHOD

CROSS-REFERENCE TO RELATED APPLICATIONS

This application is a continuation of international application number PCT/EP2006/011151, filed on Nov. 21, 2006, the contents of which is incorporated by reference herein in its entirety and for all purposes.

FIELD OF THE INVENTION

The present invention relates to an at least partially resorbable implant for long bones for treating bone fractures and a treatment method for (clean) fractures of long bones. Because of the partial resorptivity of the implant, at least a part of the implant can remain in the long bones and as a result of this an additional operation for removal of the implant after the fracture has healed can be avoided.

BACKGROUND OF THE INVENTION

Fracture of the clavicle, i.e. the collarbone, is one of the most frequent fractures in humans (20 to 25% of all fractures in children and 5 to 15% of all fractures in adults). About 80% of clavicle fractures are shaft fractures. These fractures are usually treated conservatively by immobilisation in a sling for approximately 6 weeks. However, besides the considerably troublesome side-effects of the sling in some instances, e.g. disturbance of circulation/neurology as a result of plexus compression, both the functional and cosmetic long-term results in adults are unsatisfactory in some instances due to healing in the wrong position ("mal-union") or pseudarthrosis ("non-union") and prominent callus formation. Therefore, in the case of fractures of the shaft of the clavicle with an initially pronounced wrong position surgical stabilisation is increasingly performed. In this case, plate osteosynthesis is applied as "gold standard". Alternatively, the clavicle fracture can be treated using an intramedullary nail. The advantages and disadvantages of the respective form of osteosynthesis are shown in the following table:

| Implant | Advantages | Disadvantages |
| --- | --- | --- |
| Plate osteosynthesis | high primary stability anatomical resetting mostly possible | large wound (at least 3 screws per fracture → wound length > 6 cm) substantial devastation in the fracture region and therefore disruption of the healing of the fracture and risk of pseudarthrosis therefore, removal of metal only possible after 18 months at the earliest extramedullary transfer of force plate directly under the skin is generally found to be disturbing and painful in the case of certain activities: e.g. when carrying a backpack, playing an accordion etc. removal of metal only possible under full narcosis, in turn associated with correspondingly high operative trauma and reduced patient comfort |
| Intramedullary nail (e.g. TEN or Thalon) | little operative trauma: small incision medial clavicle, additional incision over fracture region for open resetting, if necessary | less primary stability, in particular no compression onto fracture risk of secondary dislocation and pseudarthrosis ("non-union") and implant migration (life-threatening in some instances!) removal of metal generally only possible under full narcosis, in turn associated with correspondingly high operative trauma and reduced patient comfort |

In order to obtain a high primary stability by way of a minimally invasive access while achieving vascularisation in the fracture region and, moreover, to also allow metal to be removed under local anaesthesia, a completely new osteosynthesis principle is to be developed that can be applied in particular in the case of a clavicle fracture, but also in principle to other long bones.

There are already advanced approaches in the use of non-rigid connecting elements for the treatment of joint injuries.

A simplified joint-bridging implant in the case of bone fractures close to the joint, but in particular in the case of joint dislocations, is illustrated in DE 36 30 138 A1. In DE 36 30 138 A1 steel cords are used in this case to allow an elastic connection of joint parts. Two anchor parts are provided, one of which is respectively secured to the bone or joint part and both anchor parts are articulated to one another, wherein the connection is formed by at least one cord. However, DE 36 30 138 A1 is merely aimed at a flexible connection in the case of joint fractures, and a rigid connection of a broken long bone is not disclosed. The implant is not resorbable and not for implantation in a minimally invasive manner.

For a joint-bridging implant DE 196 18 552 A1 proposes to drive a bone segment by a tensile force generated in a cord by flexion of the healthy bone articulated in the joint and caused to act directly or indirectly on the segment by said cord in an intermedullary arrangement by means of an intramedullary nail in order to transport the segment autoinductively using a complete implanted device to bridge a bone defect on a long bone. Transverse pins are necessary to stabilise the intramedullary system. However, the set problem and the proposed approach for solution are likewise not readily transferable to the case of bones broken with clean fractures. Moreover, the implant is not resorbable and not for implantation in a minimally invasive manner.

DE 1 852 874 U shows an implant for connecting two parts of a broken long bone, wherein the implant is formed by a shaped piece that is intended for insertion into the medullary cavity of a broken long bone. The shaped piece has a through-opening with a constant inside diameter that extends through the entire shaped piece. The implant must function without tension, as a result of which no fracture compression is achieved. Moreover, transverse pins are required to stabilise the intramedullary system. Furthermore, DE 1 852 874 U does not disclose a resorbable material or a minimally invasive implantation.

U.S. Pat. No. 6,045,551 discloses an implant running transversely to the bone axis for the tension-resistant connection of two parts of a broken long bone, wherein the implant has two anchor parts, a cord and a shaped piece, wherein the anchor parts can be secured to the one cord, wherein the shaped piece has a through-opening, through which the cord is guided so that the shaped piece extends around the cord between two anchor parts. Since a plurality of cord anchors are required, the implant is not implanted in a minimally invasive manner and no simplification of the operation or reduction in operating time is achieved.

DE 824 377 relates to a non-resorbable device for pulling together the fractured ends of a broken long bone by means of a pulling member, which is to be inserted at a spacing from the fracture site and has an anchor that lodges against the bone wall with a pull. However, DE 824 377 does not disclose a tubular implant that could prevent a translatory dislocation tendency of the bone ends.

EP 0 428 985 A1 describes an intramedullary nail that can be secured in a long bone by means of a wire loop, wherein the primary aim of EP 0 428 985 A1 is simplified distal locking. However, transverse pins must be inserted both in the proximal and the distal end of the fractured bone for stabilisation of the intramedullary system, and these, like the intramedullary nail itself, are not resorbable.

A resorbable osteosynthetic element is described in FR 2 721 818. It consists of an anchor, an elastic cord, a tensioning device and a fastening. One end of the cord is secured to the anchor, while the other is connected to the tensioning device and the fastening after it has been pulled through-holes that have been drilled into the two bone parts. The anchor is secured to the surface of one bone fragment, while the tensioning device and fastening are secured to the surface of the other bone fragment. However, FR 2 721 818 does not disclose a shaped piece that can be inserted into the medullary cavity of a broken long bone to ensure a secure fixture of the cord.

Further bio-resorbable systems for insertion in bones are described in U.S. Pat. No. 6,096,060, which describes an anchor system for securing soft tissue to the bone, and in U.S. Pat. No. 5,470,334, which describes a bone fixing screw. However, neither system is suitable for the treatment of clavicle fractures.

It is therefore desirable to have an implant available that allows the fractured pieces of a long bone to be stabilised by an implant with less expenditure than previously.

It is additionally desirable to have an implant available that allows the removal of the implant after biological union to be substantially simplified.

An aim is to have an operating technique available that allows a surgical intervention for implanting and removing an implant to be simplified.

In addition, as in all surgical procedures, the aim is to achieve a gentle operation with only slight blood loss and small wound surface, while still providing a stable fracture treatment.

SUMMARY OF THE INVENTION

According to a first aspect of the present invention, an implant is provided for connecting two parts of a long bone that has broken with a substantially smooth break, i.e. not a splintered fracture. In this case, the implant is formed by a shaped piece, which is adapted to be inserted into the medullary cavity of the broken long bone. In this case, the shaped piece has at least one through-opening with a substantially constant inside diameter extending substantially through the entire shaped piece. The shaped piece is formed from a resorbable material (cf. claim 1).

This means that the shaped piece can be inserted into the medullary cavity of a long bone in a similar manner to an intramedullary nail. In contrast to a "normal" intramedullary nail, the shaped piece according to the present invention is provided with a through-hole that allows a wire or where appropriate a resorbable cord to be pulled through the shaped piece. If in this case the wire is secured at the ends of the bones and tensioned, screws are completely unnecessary for securing the shaped piece.

In this case, the shaped piece is adapted to exploit the principle of an internally braced stack in order to press the fracture surfaces of a long bone against one another. This principle is known, for example, in the technology of pre-stressed concrete bridges, Bowden cables or rollable bars.

It must also be mentioned that the shaped piece can be formed from an elastic semi-rigid or rigid material. An elastic or semi-rigid embodiment is preferred so that the shaped piece can be inserted into the medullary cavity more easily. Moreover, an elastic or semi-rigid embodiment of the shaped piece has the advantage that the shaped piece can adapt individually to the inside surface of the bone.

In an exemplary embodiment, the shaped piece is made from a resorbable material in order to prevent the shaped piece from having to be removed from the medullary cavity again, which would require a complicated operation after healing of the bone fracture has occurred.

According to another aspect of the present invention, an implant for the tension-resistant connection of two parts of a long bone that has broken with a largely smooth break is provided. In this case, the implant has at least two anchor parts, at least one cord and a shaped piece. In this case, the anchor parts can be secured to the at least one cord. However, it is also proposed that an anchor part is already secured to the cord from the outset. The shaped piece is provided with at least one through-opening, through which the cord is guided so that the shaped piece extends around the cord between two anchor parts.

The principle of an internally braced stack is to be exploited with the present invention in order to press the fracture surfaces of a long bone against one another. This takes advantage of the fact that in the case of a clean fracture in a marrow bone a cord running in the medullary cavity would extend during flexion. If the cord is tensioned, it can no longer extend and the flexion can be prevented.

The anchor parts are intended for securing the cord to the bone. In a simple embodiment, the anchor parts can be simply configured as only thickened areas or end nipples, as is known from "bicycle Bowden cables". If the cord is guided into the medullary cavity of a bone through a small hole or a narrow slot, the cord can be securely anchored to the bone by a thickened area or a nipple at the end. However, it is also possible, for example, to use screwed anchor plates, a screw anchor or a small (possibly resorbable) plate (comparable with a shirt button) with at least one hole, through which the cord is threaded and secured. However, the use of anchoring elements more complex than nipples, for example, is not absolutely necessary. In the case of more complex fractures it is also conceivable to use a screwed plate as anchor part on a comminuted fracture section, and to stabilise a (substantially) clean fracture in another section with the implant of the present invention. An anchor part can be detachably secured to the cord.

It should also be noted that the cord is held at a respective end by an anchor part and can be laid once or multiple times. It is thus also possible, in principle, to use a plurality of implants on one fracture, which can enable even larger hollow bones to be stabilised.

In an exemplary embodiment, the cord is a steel cord that is plaited or braided from individual fibres. It should not be necessary to mention that the used materials that are used for the components of the implant (or its surfaces) should or must be physiologically compatible. The use of other materials and/or metals may also be considered. Use of a plastic or a resorbable material for the cord may also be considered. The use of titanium or platinum, for example, for the cord may likewise be considered.

In another exemplary embodiment of the present invention, the shaped piece is substantially cylindrical. In the case of a cylindrical shaped piece, an extruded tube can be used as shaped piece, for example. In the cylindrical embodiment the shaped piece can serve to hold the cord further away from the rotation or flexing point of the long bone, which allows the cord to be thinner in configuration.

Configuring the shaped piece as a cylinder with non-circular cross-section may also be considered. This implant could thus be used, for example, for non-circular long bones. The cylindrical shaped piece can be provided with rounded or conically extending ends.

In a further exemplary embodiment the shaped piece is substantially in the form of a spindle. The insertion of the shaped piece between the fracture surfaces into the medullary cavity of the bone to be provided with the implant can be simplified as a result.

Adapting the largest diameter of the substantially spindle-like shaped piece to the thickest location on the inside diameter of the bone at the fracture site can likewise be considered. It is also possible to adapt the shape of the cross-sectional surface at the largest diameter of the substantially spindle-like shaped piece to the shape of the cross-sectional surface of the cavity of the bone at the fracture site. This could be achieved, for example, by using different preformed or specially cut shaped pieces. The selection or production data can be obtained on the basis of imaging processes from a tomographic imaging machine. Because of the spindle form, the shaped piece can be aligned with the fracture surfaces at the fracture site transversely to the longitudinal direction of the bone.

The shaped piece can be provided with a structure on the outer surface, in particular with longitudinal grooves or transverse grooves. As a result of longitudinal grooves the shaped piece is provided with a substantially star-shaped cross-section. As a result of the grooves or webs the shaped piece can mesh with the inside surface of the bones. As a result of the intermeshing of the shaped piece into the inside surface torsional forces at the fracture site can be absorbed or neutralised.

The shaped piece is formed from a resorbable material. This enables the shaped piece to remain in the long bone even when the cord and the anchoring pieces have already been removed again. Because of the selection of a resorbable material no long-term compatibility of the shaped piece material is necessary. Moreover, the shaped piece does not have to be removed from the body, since the body assumes this task itself. The selection of the resorption rate of the shaped piece should be made so that the shaped piece does not break down or does not break down significantly more quickly than the bone mass knits together. The selection of the material of the shaped piece can also be matched directly to the age or the metabolic rate of the respective patient.

In a particular embodiment, the resorbable material is selected from the group comprising polyglycolide (PGA), glycolide copolymers, glycolide/lactide copolymers (PGA/PLA), glycolide/trimethylene carbonate copolymers (PGA/TMC) (product GORE SEAMGUARD® from bywass GmbH), stereoisomers and copolymers of polylactide, poly-L-lactide (PLLA) (product Sculptra® from Sanofi Aventis), poly-D-lactide (PDLA), poly-DL-lactide (PDLLA), L-lactide/DL-lactide copolymers, L-lactide/D-lactide copolymers, lactide/tetramethylene glycolide copolymers, lactide/trimethylene carbonate copolymers, lactide/δ-valerolactone copolymers, lactide/ε-caprolactone copolymers, polydepsipeptide (glycine-DL-lactide copolymer), polylactide/ethylene oxide copolymers, asymmetrically 3,6-substituted poly-1,4-dioxane-2,4-diones, poly-β-hydroxybutyrate (PHBA), PH BA/β-hydroxyvalerate copolymers (PHBA/PHVA), poly-β-hydroxypropionate (PHPA), poly-β-dioxanone (PDS), poly-Δ-valerolactone, poly-Δ-caprolactone, methyl methacrylate-N-vinyl pyrrolidone copolymers, polyester amides, oxalic acid polyesters, polydihydropyrans, polyalkyl-2-cyanoacrylates, polyurethanes (PU), polyvinyl alcohol (PVA), polypeptides from α-amino acids, poly-β-maleic acid (PMLA), poly-β-alkanoic acids, polyethylene oxide (PEO), chitin polymers, calcium hydroxide apatite or tricalcium phosphate (product Biobase® from Zimmer dental).

The shaped piece can be made from a biodegradable and resorbable surgical material that can be molecularly oriented and have a bending strength of $1.6 \times 10^3$ to $2.5 \times 10^5$ kg/cm$^2$, a flexural modulus of $5.5 \times 10^2$ to $24.0 \times 10^2$ kg/mm. It is possible that the material of the shaped part has a crystallinity of 10 to 60% and an average viscosity of the molecular weight, which amounts to 300 000 to 600 000 before a melting treatment and to 200 000 to 400 000 after a melting treatment. The weight ratio of lactic acid/glycolic acid of the copolymer can amount to 99:1 to 75:25 in this case.

In a further exemplary embodiment of the present invention, the shaped piece is composed from individual tubular or spindle-like sections, which are slid into one another at least in some sections. As a result of this, an individual e.g. spindle-like shaped piece can be composed of individual tubular sections. It is also possible to provide a "kit" for different long bones from a plurality of different resorbable tubes (i.e. shaped bodies) slid one on top of the other.

In another exemplary embodiment, the shaped piece is produced from sections composed of resorbable material that have different resorption rates. This enables the shaped piece to be slowly broken down during bone growth, for example, because of a slowly resorbable outer layer. When the outer layer has broken down, the inner core can break down quickly after the bone has healed.

The cord can also be cast into the material of the shaped piece. This can greatly simplify the use of the implant, since the operating surgeon or the user of the implant can no longer forget to thread the shaped piece onto the cord.

In a further exemplary embodiment of the implant, the shaped part has at least two further holes, which extend substantially transversely to the longitudinal direction of the shaped piece. A cord secured in the cortex layer with anchors can be directed out "forwards" to the operating surgeon and can then be tensioned and tied by the operating surgeon. It is also possible to secure the fracture site in this way with two cords and four anchor pieces that cross only slightly. It is possible that the shaped piece has two perforations in the central region, through which the lateral or medial end of the cord or wire that are already secured in the lateral or medial cortex layer with anchors can be directed out forwards, tensioned and tied.

In a further exemplary embodiment of the implant, the shaped piece has a mesh surface. If necessary, the shaped piece can be provided with a mesh of resorbable material on the surface for better stabilisation of the fracture site.

In another exemplary embodiment of the implant, the end of the shaped piece is thickened. This embodiment forms a resorbable intramedullary nail with a through-hole in longitudinal direction. The shaped piece can project out of the bone on one side, at which it is thickened, like an intramedullary nail. A cord with two anchors or anchor pieces can be pulled through the through-hole. An anchor can anchor the cord directly to or in the thickened shaped piece. The thickened part can act as a nail head in this case, which prevents the shaped piece from being pulled into the bone. In this embodiment, the shaped piece shaped like an intramedullary nail has a through-hole in the longitudinal direction, through which a cord can be pulled.

According to another embodiment of the present invention, a resorbable intramedullary nail can be provided to connect two parts of a broken long bone, wherein the intramedullary nail has a thickened region at one end and a fastening means for a cord at the other end. The thickened region in this case serves as a nail head, which prevents the nail from sliding further into the medullary cavity. The thickened region can be configured as a flat head, round head, oval head or countersunk head. The fastening means for a cord can be configured as a through-hole in the longitudinal or transverse direction, as clamping jaws, a screw thread, an eyelet or the like. A cord loop can be pulled through a transverse hole or an eyelet. The clamping jaws can be self-locking in configuration. The screw thread can serve to secure a cord running out into a threaded piece to the intramedullary nail.

In addition, the resorbable intramedullary nail can be provided with a screw thread on the upper shaft region for better anchorage of the intramedullary nail. The intramedullary nail can be pulled into the medullary cavity of a bone on the cord, so that the bone pieces are pressed onto one another at the fracture sites. In this case, the "nail head" and an anchor piece anchor the implant at the respective bone ends.

If necessary, the shaped piece also has a nail-like shape with a fastening means for a cord at the nail tip. This fastening means can be configured as an eyelet, clamping jaws or screw fastening. The shaped piece can be configured with or without a longitudinal cavity.

After the nail shaped piece has been inserted into the medullary cavity of the bone, the cord can be fastened. The cord can be tensioned in the described manner and secured on the opposite side with an anchor.

In an exemplary embodiment, the resorbable intramedullary nail is provided with a cord on the cord fastening means. The cord can be cast into the material of the intramedullary nail, for example. As a result, an additional step in the implantation of the intramedullary nail can be omitted.

The intramedullary nail or the shaped part with an integrated anchor is configured so that the cord is only attached or inserted at one end of the shaped piece and outside the cortex layer can be tensioned by means of a second anchor and "sealed".

According to another aspect of the present invention, a method for implanting an implant for connecting the parts of a broken long bone is provided. In this case, the implant comprises two anchor parts, a cord and a resorbable shaped piece. The anchor parts can be secured to at least one cord. The shaped piece has at least one through-opening, through which the cord can be guided so that the shaped piece extends around the cord between two anchor parts.

The method comprises forming or drilling a first opening in the first part of the broken long bone that runs inside the long bone from a first end region of the long bone through the wall of the long bone to the fractured end. In addition, a second opening is formed in a second part of the broken long bone that runs inside the long bone from a second end region of the long bone through the wall of the long bone to the fractured end.

In addition the method comprises threading the cord and the shaped piece through the first opening, wherein the cord runs through the shaped piece.

The method additionally comprises threading the cord through the second opening, so that the shaped piece is threaded onto the cord between the fracture surfaces of the long bone. It is possible in particular in this case (if the first opening is large enough) to pull the shaped piece through the first opening from the first end of the bone into the medullary cavity in the direction of the fracture surfaces.

In the method the shaped part can also be inserted into the medullary cavity of the long bone through the second opening or through the fracture surfaces.

In the method the cord is pulled taut and secured to the bone with anchor parts.

In the method the cord is secured at the first end region of the long bone by means of a first anchor part.

Finally the cord is pulled taut and secured at the second end region of the long bone by means of a second anchor part.

It should be noted that the anchor parts can be of different size if the first opening is larger than the second opening, for example.

It should be noted that the above method can be easily modified by changing the sequence.

However, it is also conceivable to conduct the entire operation in a closed reduction through only a small operation access point at the end region of the first or second part of the long bone.

It is thus clear that ultimately only the sequence of most of the method steps can be interchanged.

Depending on the state of the bone, the formed opening can be pierced, drilled or milled from the fracture site through the medullary cavity to an (unbroken) end region of the long bone and there through the wall of the long bone. It is also possible to conduct the drilling in the opposite direction. The opening can be drilled, pierced, milled or generated by any other means. The opening can run straight or be provided at least partially curved.

It can be necessary to make the opening through the bone wall before the end region of the bone. Therefore, the end region of the bone is explicitly defined as a region that does not lie directly at the fracture site and provides adequate possibilities for fastening for the anchor piece.

The cord is intended to run in the interior of the medullary cavity. To enable the cord to be removed again later, it is provided that at least one anchor piece is secured to the cord so that it can be easily separated from the cord.

This method can render it unnecessary to open the skin in the fracture region and expose the fracture surfaces. This method can be applied in particular if a closed reduction (repositioning) of the bone fracture succeeds. The implant can be inserted after opening the skin and drilling a hole via the medial or lateral bone end. The inserted implant is then tensioned and the cord ends anchored, and the skin closed over the incisions.

Since the ends of the collarbone can splay out in a trumpet shape, it is also possible in the case of a clavicle fracture to push a self-locking intramedullary anchor with attached cord forward from the fracture end to tension the shaped piece to the medial and/or lateral (i.e. to the bone end), position it, actuate the self-locking mechanism of the anchor and pull the cord taut to proceed with the operation. Therefore, an opening of the wall of the bone end would not be necessary. The operation is simplified and the operating time reduced as a result of this. This intramedullary anchor principle can be applied at least at one of the two bone ends.

According to another exemplary embodiment, a method for implanting an implant for connecting the parts of a broken long bone is provided. In this case, the implant comprises two anchor parts, a cord and a shaped piece. The anchor parts can be secured to at least one cord. The shaped piece has at least one through-opening, through which the cord can be guided so that the shaped piece extends around the cord between two anchor parts.

In this case, the method can comprise exposing the first fracture end of a first part of a long bone that has broken with a substantially smooth break and exposing the second fracture end of a second part of the long bone that has broken with a substantially smooth break. The method can additionally comprise forming or drilling a first opening in the first part that runs from the fracture end inside the long bone to a first end region of the long bone and there through the wall of the long bone, and forming a second opening of a second part that runs from the fracture end inside the long bone to a second end region of the long bone and there through the wall of the long bone.

In addition, the method further comprises threading the cord through the first opening, threading the cord through the shaped piece and threading the cord through the second opening. The threading is conducted so that the shaped piece is threaded onto the cord between the fractured surfaces of the long bone.

In this embodiment of the method, the shaped part is inserted into the medullary cavity of the long bone through the fracture surfaces.

In the method the cord is secured to the first end region of the long bone by means of a first anchor part.

The cord is then pulled taut and secured to the second end region of the long bone by means of a second anchor part.

It should be noted that the above method can be easily modified by changing the sequence.

Thus, for example, the first fracture end can be exposed first and then the first opening can be drilled into the first part of the long bone and through the wall of the long bone. The cord can then be threaded through the first opening and the shaped piece. The shaped part is then inserted through the fracture surfaces into the medullary cavity of the first part of the long bone, or the cord can firstly be secured to the first end region of the long bone by means of a first anchor part.

However, it is also conceivable to conduct the entire operation in a closed reduction through only a small operation access point at the end region of the first or second part of the long bone.

It is thus clear that ultimately only the sequence of most of the method steps can be interchanged.

It should also be noted that the specified methods can also be generally suitable for non-medical purposes and non-veterinary purposes such as, for example, for the extended corpse preparation in the case of accidental death or preparation in general. This special application of the present method in this special case cannot be considered as a treatment of the body, since in the case of a body that is already dead no therapeutic treatment is possible within the law, since this special "post mortem" case of application cannot be considered a treatment that serves to heal, relieve or eliminate or to alleviate the symptoms of a disorder or weakness in function of the human or animal body, or that is suitable for preventing or reducing the risk of them becoming incapacitated. It is also possible to use the method and the implant for training doctors using preparations or simulators or animal bones.

Depending on the state of the bone, the formed opening can be pierced, drilled or milled from the fracture site through the medullary cavity to an (unbroken) end region of the long bone and there through the wall of the long bone. It is also possible to conduct the drilling in the opposite direction. The opening can be drilled, pierced, milled or generated by any other means. The opening can run straight or be provided at least partially curved.

It can be necessary to make the opening through the bone wall before the end region of the bone. Therefore, the end region of the bone is explicitly defined as a region that does not lie directly at the fracture site and provides adequate possibilities for fastening for the anchor piece.

The cord is intended to run in the interior of the medullary cavity. To enable the cord to be removed again later, it is provided that at least one anchor piece is secured to the cord so that it can be easily separated from the cord.

In an exemplary embodiment of the present invention the shaped piece is made from a resorbable material.

In a further exemplary embodiment, the method additionally comprises aligning the shaped piece during insertion of the shaped part through the fracture surfaces into the medullary cavity of the long bone. A shaped piece with adapted cross-section, for example, can thus be aligned precisely before the bone ends are joined together. When using a shaped piece with adapted cross-section, alignment can be achieved both in longitudinal direction and at an angle in axial direction.

In the method, the shaped part is inserted through the fracture surfaces into the medullary cavity of the long bone, wherein one half of the shaped part should extend into the first part and the other half of the shaped part should extend into the second part of the long bone.

In a further exemplary embodiment, it can comprise making incisions to expose the fracture sites and the openings at the location of the end regions, at which the opening runs through the wall of the long bone. As a result, the respective working areas can be exposed in the case of fractures that are not open. In the case of the proposal to direct the drill hole from the fracture site, the skin can already be penetrated by the drilling tool at the exit location, and exposure of the exit location is then also useful.

If the drill hole is directed from the end region to the fracture site, the drilling location can be exposed beforehand in order to avoid complications and prevent blood vessels and nerve paths from being destroyed by the drill.

An exemplary embodiment of the method also provides closing the incisions after the cord is pulled taut and secured.

According to a further aspect of the present invention, a method for removing an implant described in the above description is provided. If the cord is also made of resorbable material, then the removal of material only relates to the anchor pieces. If the cord and the anchor pieces are made of a resorbable material, a removal of material can be completely omitted.

The method comprises specifically: exposing the first anchor part and exposing the second anchor part. The method additionally comprises detaching the first or the second anchor part from the cord. The method additionally comprises removing the cord by pulling the detached end of the cord through the wall of the long bone, through the medullary cavity and through the through-opening of the shaped part and through the wall of the long bone. The shaped piece possibly remains in the medullary cavity of the long bone in this case (unless it has already been resorbed).

The first or the second anchor part can be separated from the cord by releasing a screw or simply by severing the cord between the anchor piece and the bone.

The detachment of the first or the second anchor part can also include removal of the anchor part from the bone itself.

The detached end of the cord can be pulled through the wall of the long bone by gripping and pulling it tight at the other undetached anchor part.

Upon removal of the cord the shaped piece can already be completely or partially resorbed, and in this case remains in the medullary cavity of the long bone, in which location it is then (further) resorbed.

In an exemplary embodiment the exposure of the anchor parts includes making incisions (through the skin lying over the anchor parts) and also closing the incisions after removal of the cord (and removing the anchor pieces).

The shaped piece in particular enables the cord or the wire to be pulled out of the bone without any further complications and without any additional injuries to the medulla.

After about 9 to 18 months after insertion of the implant, the cord and the anchor pieces can be removed. For this, the anchor pieces are exposed at both ends of the cord. Exposure can be conducted through incisions into the skin of approximately 10 mm in each case. The wire lock or anchor piece can be separated (nipped off) at one end of the cord. The cord can then be pulled out at the opposite anchor piece. The incisions can then be closed with a skin suture or similar.

According to another aspect of the present invention, a method for implanting an implant for connecting the parts of a broken long bone is provided. In this case, the implant comprises an intramedullary nail with a thickened region at one end and a fastening means for a cord at the other end, a cord and an anchor part.

The anchor part can be secured to the at least one cord. The cord can be secured to the fastening means of the intramedullary nail. The cord can thus extend between an anchor part and the intramedullary nail.

In this case, the method comprises making accessible the first bone end of a first part of a long bone that has broken with a substantially smooth break and additionally making accessible the second bone end of a second part of the long bone that has broken with a substantially smooth break. A first opening is formed in the first bone end of the first part that runs inside the long bone from a first end region of the long bone and there through the wall of the long bone in the direction of the fractured end of the long bone. This opening can also extend beyond the fractured end and partially into the second part of the bone. It is also possible to form this opening from a fractured end (made accessible) and through the bone.

A second opening is formed in a second part of the long bone that runs from a second end region of the long bone, through the wall of the long bone in the direction of the first end region of the long bone. It should be explicitly noted that the sequence in which the first and the second opening are respectively made in the bone is immaterial. In principle, both openings could also be made simultaneously, or the second opening could be made before the first opening. The terms first opening and second opening in the case of the nail (with nail head) here respectively mean only the dimensions of the openings, wherein the first opening can receive the intramedullary nail and the second opening can be smaller to only receive the cord.

The intramedullary nail is threaded through the first opening or inserted into the first opening, possibly after a cord secured to the intramedullary nail has been threaded through the first opening. However, securing the intramedullary nail to the cord in the region of a (possibly opened) fracture site, and therefore not threading the cord through the first opening, may also be considered. In this case, it is also conceivable to form one opening from the bone end and one opening from the fracture site.

The cord is threaded through the second opening. The cord can also firstly be threaded through both openings and secured to the intramedullary nail, as a result of which the intramedullary nail can be pulled through the bone at the cord.

The intramedullary nail is inserted or pushed further into the bone through the first opening and through the fracture surfaces in the direction of the second end region of the long bone.

The intramedullary nail is secured at the thickened region to the first end region of the long bone. This fastening can be conducted, for example, by pulling the thickened end tightly against the bone.

The cord is tensioned or pulled taut and secured at the second end region of the long bone by means of a second anchor part. This method functions without opening the bone fracture site.

According to a further embodiment of the present invention, a method for implanting an implant for connecting the parts of a broken long bone is provided. In this case, the implant comprises an intramedullary nail with a thickened region at one end and a fastening means for a cord at the other end, a cord and an anchor part.

The anchor part can be secured to the at least one cord. The cord can be secured to the fastening means of the intramedullary nail. The cord can thus extend between an anchor part and the intramedullary nail.

In this case, the method comprises exposing the first fractured end of a first part of a long bone that has broken with a substantially smooth break, forming a first opening in the first part that runs from the fractured end inside the long bone to a first end region of the long bone and there through the wall of the long bone, exposing the second fractured end of a second part of the long bone that has broken with a substantially smooth break, forming a second opening of a second part that runs from the fractured end inside the long bone to a second end region of the long bone and there through the wall of the long bone, threading the intramedullary nail through the first opening, threading the cord through the second opening, inserting the intramedullary nail through the fracture surfaces in the direction of the second end region of the long bone, securing the intramedullary nail with the thickened region to the first end region of the long bone, tightening and securing the cord, and securing the cord at the second end region of the long bone by means of a second anchor part.

In an exemplary embodiment, the method additionally comprises securing the cord to the fastening means of the intramedullary nail. This step is only necessary if an intramedullary nail with integrated cord is not already being used. In principle, the two bone parts are threaded onto the intramedullary nail and secured on the other side by the cord and the anchor piece. The fracture site can be pressed together by the cord and the anchor piece, and this can accelerate the healing process.

BRIEF DESCRIPTION OF THE DRAWING FIGURES

The invention is explained in more detail below on the basis of exemplary embodiments of a partially resorbable implant for osteosynthesis (i.e. healing of bone fractures) for a clavicle fracture (i.e. collarbone fracture) by means of FIGS. 1 to 15.

Figure 3:
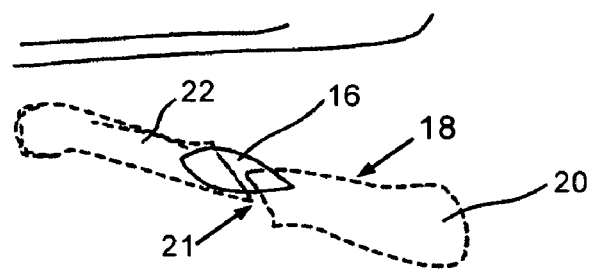

FIG. 3 schematically shows an incision over a broken collarbone using an anatomical preparation.

Figure 4:
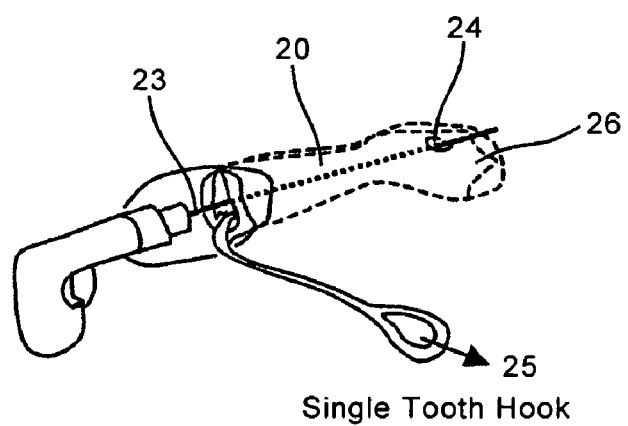

FIG. 4 schematically shows the first opening being formed in the first part of a broken collarbone using an anatomical preparation.

Figure 5:
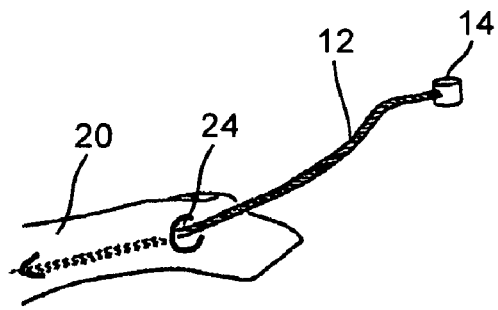

FIG. 5 schematically shows a cord with attached anchor piece being threaded through the drill hole made in FIG. 4 using an anatomical preparation.

Figure 6:
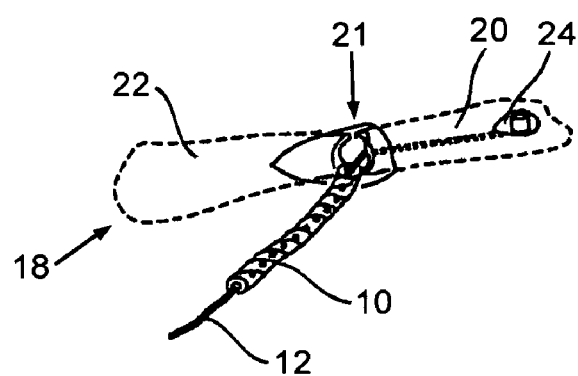

FIG. 6 schematically shows a cord being threaded through the shaped piece using an anatomical preparation.

Figure 7:
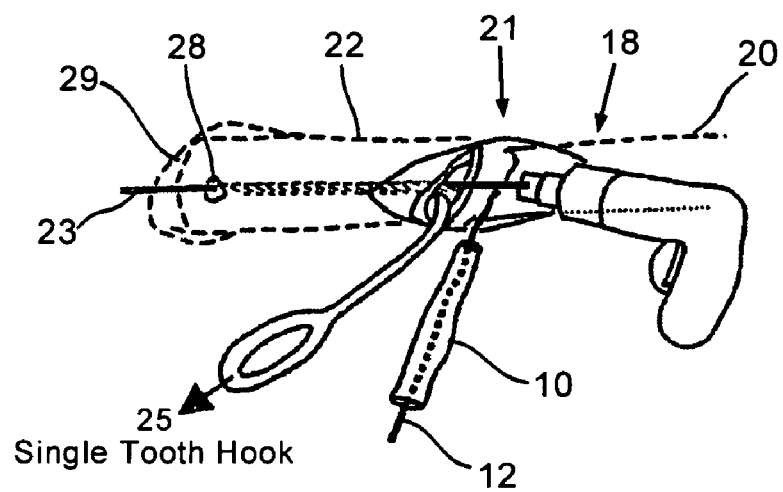

FIG. 7 schematically shows the second opening being formed in the second part of a broken collarbone using an anatomical preparation.

Figure 8:
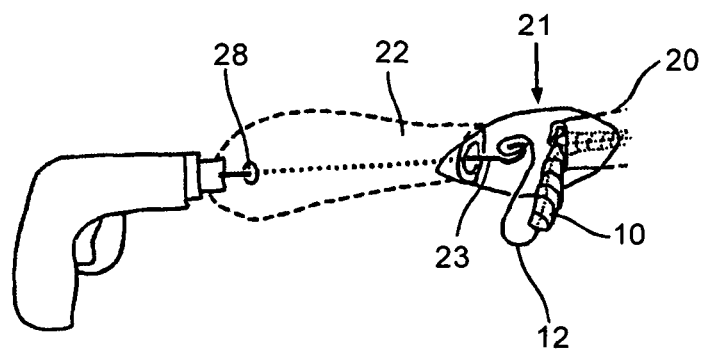

FIG. 8 schematically shows a cord being threaded through the drill hole made in FIG. 7, which can correspond to a resetting of the hollow drill, using an anatomical preparation.

Figure 9:
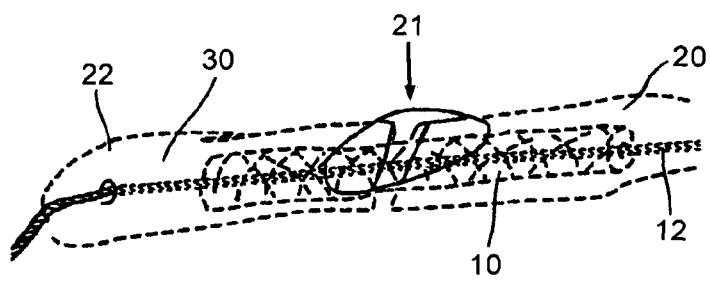

FIG. 9 schematically shows the cord threaded through and the shaped piece inserted into the medullary cavity using an anatomical preparation.

Figure 10:
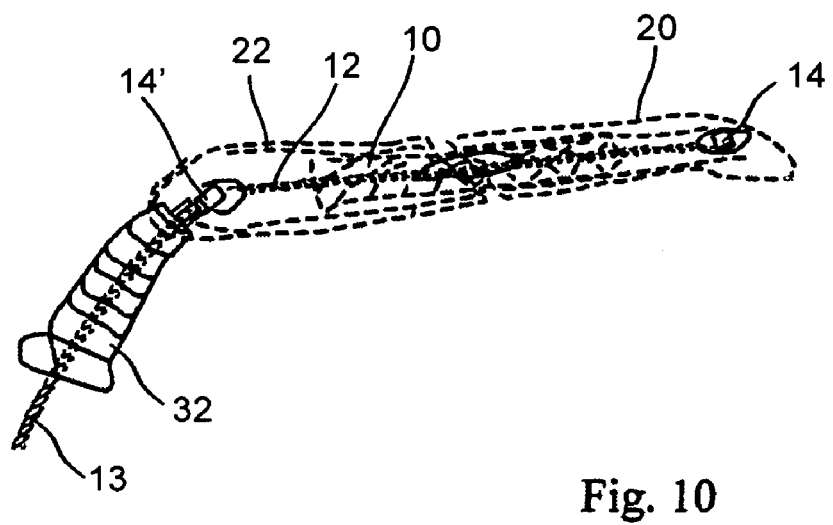

FIG. 10 schematically shows the cord being pulled taut and the second anchor piece being attached to the cord using an anatomical preparation.

Figure 11A:
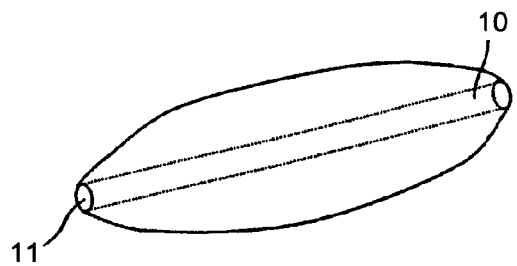
Figure 11B:
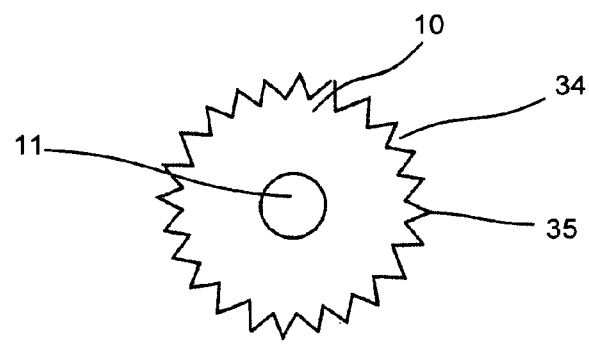

FIGS. 11A and 11B are two schematic views of a shaped piece with a substantially star-shaped cross-section.

Figure 12:
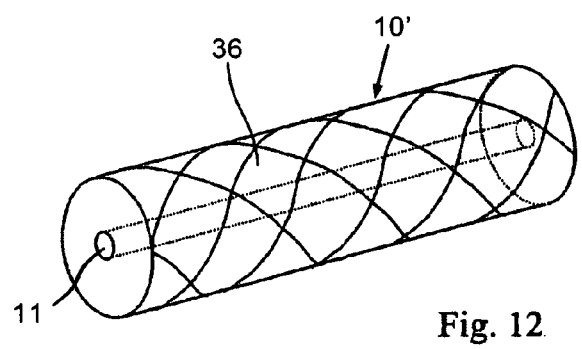
Figure 13:
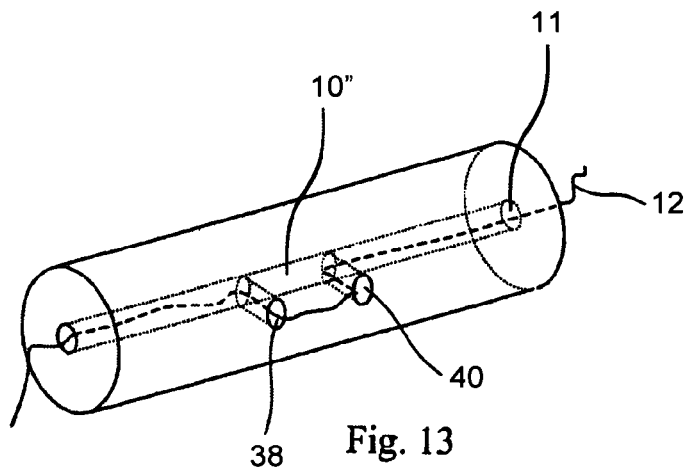
Figure 14:
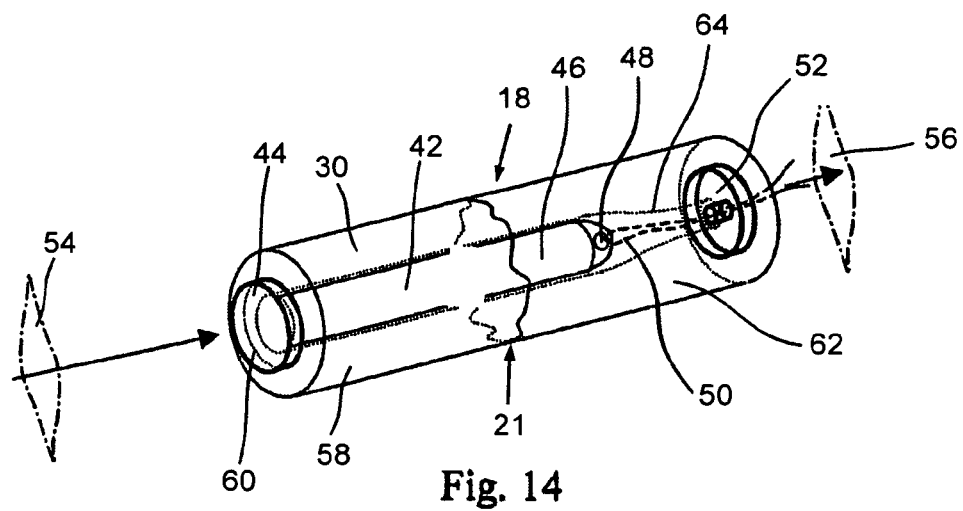

FIGS. 12-14 are schematic views of different embodiments of shaped pieces (FIGS. 12 and 13) and intramedullary nails (FIG. 14) according to the invention.

DETAILED DESCRIPTION OF PREFERRED EMBODIMENTS OF THE INVENTION

Although the invention illustrated and described herein with reference to specific embodiments, the invention is not intended to be limited to the details shown. Rather, various modifications may be made in the details within the scope and range of equivalents of the claims and without departing from the invention.

To illustrate the present invention and illustrate the use of the invention, the invention is used on a collarbone fracture here by way of example. However, it is clear that the invention can be used, in principle, in any type of substantially clean fractures of long bones.

Collarbone fractures are usually treated conservatively by immobilisation in a sling for approximately 6 weeks. In addition to the considerably troublesome side-effects of the sling in some instances, this can result in the bones knitting together in the wrong position.

Collarbone fractures with initially significantly pronounced wrong positioning are therefore increasingly being stabilised be surgical procedure. In this case, conventionally, the broken ends are joined by a screwed plate, i.e. using "plate osteosynthesis". Alternatively, collarbone fractures can also be joined by an intramedullary nail.

Figure 1:
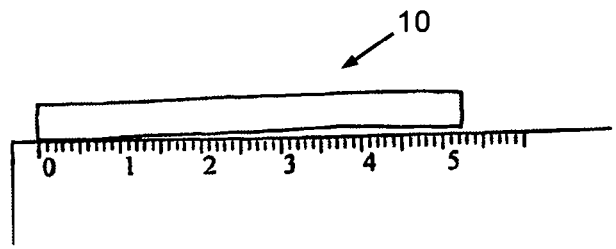
FIG. 1 represents a shaped piece according to an embodiment of the present invention.

FIG. 1 represents a shaped piece 10 according to an embodiment of the present invention.

The implant substantially comprises two parts and is therefore very easy to handle during surgery, wherein modifications are possible.

The first part consists of a resorbable shaped piece 10 that is configured in FIG. 1 as a tube. The tube is resorbable. The shown tube 10 has an (end) length of approx. 80 mm and an inside diameter of approx. 2 mm. The outside diameter amounts to approx. 4.5 mm. The resorbable tube 10 shown in FIG. 1 is designed for fractures of the collarbone. A wire, a resorbable cord or a wire cord can be threaded through the tube. The tearing and bending strength of the cord corresponds approximately to that of a conventional antenna cable. The outer surface of the resorbable tube 10 can be contoured. The dimensions and the material can be selected so that a resorption time of approx. 12 weeks or longer results.

Figure 2:
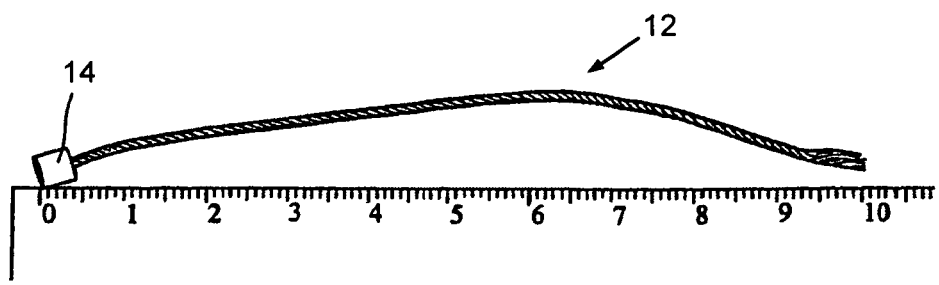
FIG. 2 is a representation of a cord with an anchor piece attached on one side.

FIG. 2 is a view representing a cord or wire 12 with an anchor piece 14 attached on one side. The wire cord 12 can be approx. 20 cm long and have a thickness or diameter of approx. 1 to approx. 2 mm. The diameter can be varied according to the case of application, i.e. the dimensions of the respective bone. The cord 12 is provided with a wire lock as anchor piece 14 at one wire or cord end. The other cord end can be secured to the bone with a further wire lock as anchor piece 14' (as shown in FIG. 10) after being pulled through the bone. In this case, a wire lock 14 can already be secured to the cord end. The second lock (i.e. anchor piece 14') is firstly threaded onto the wire 12 at the end of the operation and then closed as discussed in detail below (i.e. in a similar manner to a lead seal).

Use of a braided (multiple-strand) cord or a monofilament cord (i.e. a wire) is also provided. Use of a cord that is round or flat or band-like in cross-section is also provided. The cord 12 and/or the anchor pieces 14 can be made from resorbable material.

FIG. 3 schematically shows an incision 16 over a broken collarbone 18 using an anatomical preparation. For this, a skin incision of about 2 cm in length is made over the break or fracture site 21.

FIG. 4 schematically shows the first opening 24 being formed in the first part 20 of a broken collarbone 18 using an anatomical preparation. This can be performed by drilling into the medial fragment to approx. 4 cm with a diameter of approx. 5 mm. A single tooth hook 25 can be used to spread apart the incision for access to the drilling site prior and during drilling. This drill hole 24 can be overdrilled using a hollow drill 23 with a diameter of approx. 2 mm. This drill hole 24 penetrates the end 26 of the bone with a drilled medioventral penetration of the cortex layer. The drill hole 24 can also perforate the skin. It is possible to use a step hollow drill for this step. An approx. 5 mm long skin incision is made at the exit location of the overdrilled hole from the bone.

FIG. 5 schematically shows a cord 12 with attached anchor piece 14 being threaded through the drill hole 24 made in FIG. 4 using an anatomical preparation. The wire cord 12 can be threaded in from the medial side by means of a hollow drill 23. The wire 12 is pulled through as far as the fracture site 21. The hollow drill is removed.

FIG. 6 schematically shows a cord 12 being threaded through the shaped piece 10 using an anatomical preparation. The resorbable shaped piece 10 is drawn onto the wire or cord 12 at the fracture site 21. The resorbable shaped piece 10 is inserted into the medullary cavity of the bone 18 via the cord 12 and the fracture site 21. The resorbable shaped piece 10 can be inserted at least to the depth of the first drill hole 24 (with the diameter of 5 mm).

Use of a milling cutter or oscillating cutter is also provided to form contoured drill holes or drill holes 24 that are not round in cross-section. This can be used in particular for shaped parts profiled in the longitudinal and peripheral direction.

FIG. 7 schematically shows the second opening 28 being formed in an end 29 of the second part 22 of a broken collarbone 18 using an anatomical preparation. The second (lateral) fragment 22 of the bone 18 can be drilled to a depth of approx. 4 cm with a diameter of approx. 5 mm. This drill hole 28 can be directed further through the bone wall in a laterodorsal direction by overdrilling using a hollow drill 23 (with a diameter of approx. 2 mm). An approx. 0.5 cm long skin incision can be made at the location where the drill is guided through the bone wall.

Although the drawings show the shaped piece 10 being inserted via the fracture site 21, those skilled in the art will appreciate that a properly dimensioned shaped piece 10 could also easily be inserted through either one of the drill holes 24, 28 in either end 26, 29 of the two bone parts 20, 22.

FIG. 8 schematically shows a cord 12 being threaded through the drill hole 28 made in FIG. 7 using an anatomical preparation. The cord 12 is threaded through the bone from the side (laterally) at the fracture site 21 using a hollow drill 23. The hollow drill 23 is then removed.

FIG. 9 schematically shows the cord 12 threaded through and the shaped piece 10 inserted into the medullary cavity 30 using an anatomical preparation. In the Figures the shaped piece 10 is arranged in the medullary (intermedullary) cavity 30 and aligned. In this case, the shaped piece 10 is respectively inserted approx. 4 cm into the medullary cavity 30 of the fractured bone pieces 20, 22.

FIG. 10 schematically shows the cord 12 being pulled taut and the second anchor piece 14' being attached to the cord 12 using an anatomical preparation. The cord 12 is pulled taut by tensioning the wire cord by pulling on the lateral end 13 until the first (medial) wire lock 14 lies on the other (medial) side of the collarbone 18. The (lateral) anchor piece 14' in the form of a wire lock is then threaded on the cord 12.

After the lateral wire lock 14' is threaded on, a wire tensioner (or a cord tensioner) 32 is attached and the cord 12 is pulled taut. The precise tension results from the respective bone and fracture status. During tensioning of the cord 12 the two bone ends 20, 22 are brought together under the control of the fracture region 21. When the fracture sites 21 lie flat against one another the (lateral) wire lock 14' is firmly clamped. The wire tensioner 32 is removed and a projecting excess cord is severed or nipped off on the lateral side. The skin is then closed again at the three incisions.

It should be appreciated that the cord and the two anchor pieces will be evident in an X-ray image of the bone parts with the implant implanted therein. The resorbable shaped piece is not evident on an X-ray image. Only the curve of the wire can indicate that the cord is not resting against the inner bone wall of the medullary cavity 30. Only the two anchor pieces 14, 14' in the form of wire locks are evident in an opened anatomical preparation. The shaped piece located in the medullary cavity of the collarbone is not visible under x-ray.

After the bone fracture has healed, the cord 12 and the anchor pieces 14, 14' can be removed. For this, the skin over the anchor pieces 14, 14' is cut open. The incisions can be approx. 5 to 10 mm in each case. An anchor piece 14, 14' can be removed by severing or nipping off the cord 12 at one end. The cord 12 can then be pulled out at the opposite anchor piece. The incisions can be closed with a skin suture or the like.

FIGS. 11A and 11B show an embodiment of a substantially spindle-like resorbable shaped piece 10 in a side view (FIG. 11A) and a cross-sectional view (FIG. 11B). The shaped piece 10 can be hooked or wedged in place in the cavity of the bone by the grooves 34 or the webs or ribs 35, so that no torsional movement of the fracture ends relative to one another is possible around the longitudinal axis of the shaped piece 10. In FIGS. 11A and 11B the resorbable shaped piece 10 is provided with a through-hole or recess 11, through which the cord 12 can then be pulled for stabilisation. The two bone ends 20, 22 can be prevented from rotating relative to one another at the fracture site by the longitudinal grooves 34 and the longitudinal webs or longitudinal ribs 35. In the case of an elastic shaped piece 10, a substantially star-shaped geometry can also serve to adapt the shaped piece 10 to non-round bone inside cross-sections because the webs can be laid against one another. The outer surface of the shaped piece 10 can also be provided with fins that are curved in radial direction or also arranged in a spiral shape. It is also possible that the shaped piece is roughened on the outer surface to simplify production.

FIG. 12 shows an embodiment of a shaped piece 10' with a mesh surface 36 in a schematic view. If necessary, the shaped piece 10' can be provided with a resorbable mesh or the like on the surface to allow better stabilisation of the fracture surface.

In a schematic view, FIG. 13 shows an embodiment of a shaped piece 10" with at least two further holes 38, 40 that extend substantially transversely to the longitudinal direction of the shaped piece 10". As a result, a cord 12 secured with anchors in the cortex layer can be directed out "forwards" to the operating surgeon and can then be tensioned and tied by the operating surgeon. It is also possible to thus secure the fracture site with two cords and two anchor pieces that only cross slightly. It is possible that the shaped piece has two perforations in the central region, through which the lateral or medial end of the cord or wire that are already secured in the lateral or medial cortex layer can be directed out forwards, tensioned and tied.

FIG. 14 is a schematic view of an embodiment of an intramedullary nail 42. In this case, the intramedullary nail comprises a nail head 44, a nail shaft 46, an eyelet 48 as a fastening device for a cord 50. The intramedullary nail 42 is braced by the cord 50 and by an anchor piece 52 in relation to the bone 18, as a result of which the bone 18 broken at the fracture line 21 is pressed together at the fracture line 21.

The intramedullary nail 42 can be inserted into the bone in the direction of the arrow through a skin incision 54 indicated on the left side. The cord 50 can be tensioned in relation to the anchor piece 52 or the anchoring arrangement in the direction of the arrow through a skin incision 56 indicated on the right side. The cord 50 can be secured to the anchor piece 52 through the skin incision 56 indicated on the right side. In this case, the medullary cavity 30 of the first (left) bone piece 58 has a uniform (cylindrical) drill hole 60 as a first opening. The medullary cavity 30 of the second (right) bone piece 62 has a tapered drill hole 64 as second opening. In this case, the second drill hole 64 can be made in the second fractured bone piece 62 through the first drill hole 60, as a result of which intervention on the side of the second bone piece 62 can be kept to a reduced level.

Thus, the implant is based on an inner splinting and on an axial pull in order to achieve a more reliable healing of the fracture and an increased initial stability. When correctly attached, the implant serves to pull the broken parts of a bone together and press the fracture surfaces against one another.

However, in contrast to conventional methods, the splinting is not based on a completely rigid shaped part, but on a tightly tensioned cord or wire and a shaped part surrounding the wire. In this case, the shaped part can be supported against the tightly tensioned cord or wire. This allows a high primary stability and at the same time allows the fracture surfaces to be pressed together. The shaped part that acts as an internal splint results in a neutralisation of any shear forces that possibly occur.

The unique tensioning mechanism enables an immediate post-operative mobilisation of the collarbone probably within specific movement and stress limits with only a single operation. Because of the self-dissolving shaped part used, a substantial portion of the implant no longer needs to be removed. All these advantages are obtained with an operating method that functions with only slight blood loss and a small wound surface compared to the conventional methods. A stable fracture treatment is achieved nonetheless.

Because of the use of the present implant, the patient only has to be operated on once under full narcosis during insertion of the implant or stabilisation of the fracture. The removal of the implant after healing of the fracture (i.e. around 9 to 18 months after implantation) can be performed in an ambulant procedure under local anaesthetic. The implant thus represents a considerable simplification particularly for the patient.

By using a minimally invasive access, the formation of blood vessels is achieved in the region of the fracture, which in turn benefits the healing of the bone.

It must be indicated here once again that the implant can be used, in principle, in all orthopaedic and surgical treatments and trauma surgery for instable fractures of long bones. It is also possible to use this method and the implants of the invention in veterinary medicine.

The protective scope of this invention is determined by the patent claims and not merely by the embodiments shown in the drawing. Changes and modifications of the subject to the drawings should also be included in the protective scope, where they are covered by the wording of the attached claims. Thus, it is conceivable instead of using the wire lock or "nipple", for example, to use anchor pieces that can be nailed or screwed firmly to the bone. It is also possible to lay the cord or wire multiple times, e.g. in loops, or a plurality of shaped parts or one shaped part with a plurality of through-openings. Guide sleeves can also be provided at the location where the cord or wire passes through the bone wall.

The invention claimed is:

1. Implant for the tension-resistant connection of two parts of a long bone that has broken with a substantially smooth break, the implant comprising:

at least two anchor parts,
   at least one cord, the at least two anchor parts adapted to be secured to the at least one cord, and
   a shaped piece, the shaped piece having at least one through-opening, through which the cord is guided, so that the shaped piece extends around the cord and is completely positioned between two of the at least two anchor parts, and extends in the medullary cavity of a broken long bone in a longitudinal direction of the broken long bone,
   wherein the shaped piece is formed from a resorbable material and the two of the at least two anchor parts are secured to the cord outside of the long bone.

2. Implant according to claim 1, wherein the cord is a steel cord composed of individual fibres.

3. Implant according to claim 1, wherein the cord is made of resorbable material.

4. Implant according to claim 1, wherein the shaped piece is substantially cylindrical.

5. Implant according to claim 1, wherein the shaped piece is substantially in a form of a spindle.

6. Implant according to claim 1, wherein a surface of the shaped piece is contoured.

7. Implant according to claim 1, wherein the shaped piece is provided with longitudinal grooves or with transverse grooves.

8. Implant according to claim 1, wherein the shaped piece has a substantially star-shaped cross-section.

9. Implant according to claim 1, wherein the resorbable material comprises one of polyglycolide (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide/DL-lactide copolymers, L-lactide/D-lactide copolymers, lactide/tetramethylene glycolide copolymers, lactide/trimethylene carbonate copolymers, lactide/δ-valerolactone copolymers, lactide/ε-caprolactone copolymers, polydepsipeptide (glycine-DL-lactide copolymer), polylactide/ethylene oxide copolymers, asymmetrically 3,6-substituted poly-1,4-dioxane-2,4-diones, poly-β-hydroxybutyrate (PHBA), PHBA/β-hydroxyvalerate copolymers (PHBA/PHVA), poly-β-hydroxypropionate (PHPA), poly-β-dioxanone (PDS), poly-Δ-valerolactone, poly-Δ-caprolactone, methyl methacrylate-N-vinyl pyrrolidone copolymers, polyester amides, oxalic acid polyesters, polydihydropyrans, polyalkyl-2-cyanoacrylates, polyurethanes (PU), polyvinyl alcohol (PVA), polypeptides from α-amino acids, poly-β-maleic acid (PMLA), poly-β-alkanoic acids, polyethylene oxide (PEO), chitin polymers, calcium hydroxide apatite or tricalcium phosphate.

10. Implant according to claim 1, wherein the shaped piece is composed of individual tubular or spindle-shaped sections, which are slid into one another at least in some sections.

11. Implant according to claim 10, wherein the individual sections have a resorbable material with different resorption rates.

12. Implant according to claim 1, wherein the shaped piece has at least two further holes, which are arranged substantially transversely to a longitudinal direction of the shaped piece.

13. Implant according to claim 1, wherein the shaped piece is provided with a mesh surface.

14. Method for implanting an implant for connecting parts of a long bone that has broken with a smooth break, wherein the implant comprises:

two anchor parts,
a cord, and
a shaped piece,
wherein:
   the anchor parts can be secured to the cord, and
   the shaped piece is made of a resorbable material and has at least one through-opening, through which the cord can be guided so that the shaped piece extends around the cord and between two anchor parts,
the method comprising:
forming a first opening in a first bone part that runs in a longitudinal direction inside the long bone from a first end region of the long bone through a first wall of the long bone to a first fractured end,
forming a second opening in a second bone part that runs in the longitudinal direction inside the long bone from a second end region of the long bone through a second wall of the long bone to a second fractured end,
threading a cord and the shaped piece through one of the first opening, the second opening, the first fractured end, and the second fractured end, wherein the cord runs through the shaped piece,
threading the cord through the second opening, so that the shaped piece is threaded onto the cord between the fracture surfaces of the long bone,
securing the cord at the first end region of the long bone by means of a first anchor part, and
pulling the cord taut, and
securing the cord at the second end region of the long bone by means of a second anchor part;
wherein:
   the two anchor parts are secured to the cord outside of the long bone and once secured to the cord provide a compressive force to the first and second bone parts; and
   the shaped piece extends in a medullary cavity of the long bone between the two anchor parts.

15. Method according to claim 14, further comprising:
exposing the first fractured end of the first bone part such that the first opening into the first bone part is formed from the fractured end inside the long bone to a first end region of the long bone and through the wall of the long bone, and
exposing the second fractured end of a second bone part of the long bone such that the second opening of a second bone part is formed from the fractured end inside the long bone to a second end region of the long bone and through the wall of the long bone,
wherein the cord and the shaped piece are inserted through the fracture surfaces into the medullary cavity of the long bone by threading the cord through the first opening, threading the cord through the shaped piece, threading the cord through the second opening, so that the shaped piece is threaded onto the cord between the fracture surfaces of the long bone.

16. Method according to claim 14, further comprising aligning of the shaped piece when the shaped piece is inserted through the fracture surfaces into the medullary cavity of the long bone.

17. Method according to claim 14, further comprising making incisions to expose the fracture surfaces and the openings at the locations of the end regions where the opening runs through the wall of the long bone.

18. Method according to claim 17, further comprising closing the incisions after making the cord taut and securing the cord to the anchor parts.

19. Method for removing an implant implanted using the method according to claim 14, comprising:
exposing the first anchor part,
exposing the second anchor part,
detaching the first or the second anchor part from the cord, and
removing the cord by pulling a detached end of the cord through the first or second wall of the long bone, through the medullary cavity and through the through-opening of the shaped piece and through the other of the first or second wall of the long bone, wherein the shaped piece remains in the medullary cavity of the long bone.

20. Method according to claim 19, wherein:
exposing the anchor parts comprises making incisions, and
the method further comprises closing the incisions after pulling the cord through the bone parts.

21. Method for implanting an implant for connecting parts of a long bone that has broken with a smooth break, wherein the implant comprises:
an intramedullary nail comprising:
   a thickened region at a first end, and
   a fastening means for a cord at a second end,
a cord, and
an anchor part,
wherein:
   the anchor part is adapted to be secured to the at least one cord, and
   the cord is adapted to be secured to the fastening means of the intramedullary nail, so that the cord extends between an anchor part and the intramedullary nail,
the method comprising:
making accessible a first bone end of a first bone part of a long bone that has broken with a substantially smooth break,
forming a first opening in the first bone end of the first bone part that runs in a longitudinal direction inside the long bone from a first end region of the long bone and through a first wall of the long bone in a direction of the fractured end of the long bone,
making accessible the second bone end of a second bone part of the long bone that has broken with a substantially smooth break,
forming a second opening in a second bone part of the long bone that runs in the longitudinal direction from a second end region of the long bone, through a second wall of the long bone in a direction of the first end region of the long bone,
securing the cord at the fastening means of the intramedullary nail,
threading the intramedullary nail at least partially through the first opening,
threading the cord through the second opening,
pushing the intramedullary nail further through the first opening and through the fracture surfaces in a direction of the second end region of the long bone such that the intramedulary nail extends in the medullary cavity of the long bone,
securing the intramedullary nail at the thickened region at the first end region of the long bone,
pulling the cord taut, and
securing the cord to the second end region of the long bone by means of a an anchor part positioned outside of the long bone such that a compressive force is provided to the first and second bone part.

* * * * *